US011230611B2

(12) United States Patent
Smit et al.

(10) Patent No.: US 11,230,611 B2
(45) Date of Patent: Jan. 25, 2022

(54) BIOREFINERY OF BROWN MACROALGAE

(71) Applicant: Nederlandse Organisatie voor toegepast-natuurwetenschappelijk Onderzoek TNO, The Hague (NL)

(72) Inventors: Adrianus Theodorus Smit, Petten (NL); Wouter Johannes Joseph Huijgen, Petten (NL)

(73) Assignee: Nederlandse Organisatie voor toegepast-natuurwetenschappelijk Onderzoek TNO, The Hague (NL)

(*) Notice: Subject to any disclaimer, the term of this patent is extended or adjusted under 35 U.S.C. 154(b) by 0 days.

(21) Appl. No.: 16/765,492

(22) PCT Filed: Nov. 21, 2018

(86) PCT No.: PCT/NL2018/050783
§ 371 (c)(1),
(2) Date: May 20, 2020

(87) PCT Pub. No.: WO2019/103607
PCT Pub. Date: May 31, 2019

(65) Prior Publication Data
US 2020/0291138 A1 Sep. 17, 2020

(30) Foreign Application Priority Data

Nov. 21, 2017 (NL) .................................... 2019949

(51) Int. Cl.
C08B 37/00 (2006.01)
C07C 29/76 (2006.01)
C07C 31/26 (2006.01)
C08L 5/04 (2006.01)

(52) U.S. Cl.
CPC .......... *C08B 37/0003* (2013.01); *C07C 29/76* (2013.01); *C08B 37/0024* (2013.01); *C08B 37/0084* (2013.01); *C07C 31/26* (2013.01); *C08L 5/04* (2013.01)

(58) Field of Classification Search
None
See application file for complete search history.

(56) References Cited

U.S. PATENT DOCUMENTS

| 5,539,133 A | 7/1996 | Kohn et al. |
| 2007/0218076 A1 | 9/2007 | Michailovna et al. |

FOREIGN PATENT DOCUMENTS

| CN | 101428761 | 5/2009 |
| CN | 103755831 | 4/2014 |
| JP | 62286907 A2 | 12/1987 |
| JP | 2009225791 A2 | 10/2009 |
| RU | 2028153 | 2/1995 |
| RU | 2194525 | 12/2002 |
| WO | WO2016/157130 A1 | 10/2016 |
| WO | WO2016/157131 A1 | 10/2016 |
| WO | WO2017/081677 A1 | 5/2017 |

OTHER PUBLICATIONS

Park, KR 2007-0075274 A, Jul. 2007, machine translation. (Year: 2007).*
Wei, Trends in Biotechnology, Feb. 2013, vol. 31, No. 2, pp. 70-77. (Year: 2013).*
Black, J. appl. Chem., I, Sep. 1951, pp. 414-424. (Year: 1951).*
G. Hernandez-Carmona et al: "Conventional and alternative technologies for the extraction of algal polysaccharides" In: "Functional Ingredients from Algae for Foods and Nutraceuticals", (Jan. 1, 2013).
Wang, Tao, et al. "Antioxidant capacities of phlorotannins extracted from the brown algae *Fucus vesiculosus*." Journal of agricultural and food chemistry 60.23 (2012): 5874-5883.
Wang, Chun-Ying, and Yean-Chang Chen. "Extraction and characterization of fucoidan from six brown macroalgae." Journal of Marine Science and Technology 24.2 (2016): 319-328.
Foley, Sarah A., et al. "An unfractionated fucoidan from Ascophyllum nodosum: Extraction, characterization, and apoptotic effects in vitro." Journal of natural products 74.9 (2011): 1851-1861.
Yang, Chen, Donghwa Chung, and SangGuan You. "Determination of physicochemical properties of sulphated fucans from sporophyll of Undaria pinnatifida using light scattering technique." Food Chemistry 111.2 (2008): 503-507.
Li, Yajing, et al. "Extraction and identification of phlorotannins from the brown alga, *Sargassum fusiforme* (Harvey) Setchell." Marine drugs 15.2 (2017): 49.
Sappati, Praveen Kumar, Balunkeswar Nayak, and G. Peter van Walsum. "Effect of glass transition on the shrinkage of sugar kelp (*Saccharina latissima*) during hot air convective drying." Journal of Food Engineering 210 (2017): 50-61.

* cited by examiner

*Primary Examiner* — Layla D Berry
(74) *Attorney, Agent, or Firm* — N.V. Nederlandsch Octrooibureau; Catherine A. Shultz; Katelyn J. Bernier

(57) ABSTRACT

The present invention concerns an improved process for biorefinery of brown macroalgae, which comprises: (a) contacting the brown macroalgae with a solvent system comprising at least 30 wt % organic solvent, to obtain extracted macroalgae as solid residue and a liquor; and (b) biorefining the extracted macroalgae. The inventors have found that the contacting of step (a) results in an efficient and cost-effective dewatering of the macroalgae, wherein up to 95 wt % of the internal moisture of the macroalgae could be lost without the need for energy-consuming drying techniques. As such, the downstream biorefinery of the extracted macroalgae is greatly facilitated.

20 Claims, No Drawings

BIOREFINERY OF BROWN MACROALGAE

FIELD OF THE INVENTION

The present invention relates to an improved process for the biorefinery of brown macroalgae.

BACKGROUND ART

Seaweeds or macroalgae are a promising source of bio-based products, such as fuels and bulk chemical, because of their unique chemical composition and fast growing rates. Seaweeds are cultivated at sea, such that use of land area is minimized and depletion of nutrients in the soil is alleviated, compared to other source of biomass. Harvesting and processing seaweed is extensively discussed by McHugh in *A Guide to the Seaweed Industry* (FAO Fisheries Technical Paper No. 441, Rome, FAO, 2003, obtainable from http://www.fao.org/). Cost-effective biorefining of macroalgae is however challenging, because of their seasonal availability and high water content combined with a limited shelf life. To ensure year-round availability of seaweed for a biorefinery, seaweed must be made preservable, for example by (partial) drying or ensiling. Both conservation techniques have a major drawback. The energy demand for drying is high, since brown macroalgae have a moisture content of about 80-85% based on total weight. Ensiling is more energy efficient, but a significant part of the carbohydrates, in particular mannitol, are consumed by the lactic acid producing bacteria, such that the valorizability of the macroalgae is significantly reduced. Also downstream biorefining of the macroalgae is normally accompanied with large waste streams, wherein otherwise valuable components of the macroalgae are discarded as waste because it is economically not viable to isolate those from the waste, for example in view of the diluted nature wherein these components become available. The field of macroalgae biorefinery is gaining momentum over the last years, but complete utilization of the valuable components in seaweed in a cost-effective and sustainable manner is as yet not achieved. US 2007/0218076 describes a process wherein seaweed is extracted with an alcohol and subsequently with water. The alcoholic extract is then dried.

The present invention obviates these drawbacks of prior art macroalgae biorefinery, and provides a cost-efficient pretreatment of macroalgae, such that the pretreated macroalgae are readily available for biorefining all year round. Furthermore, the present invention provides a more cost-efficient and durable biorefining of macroalgae.

SUMMARY OF THE INVENTION

The present invention is based on the finding of the inventors that brown macroalgae experience solvent-induced dehydration by contacting the macroalgae with an organic solvent. Without being bound to a theory, it is believed that the structural matrix of the macroalgae shrinks and expels most of the internal moisture, including water-soluble compounds such as mannitol. Upon contacting, a solid phase and a liquid phase are obtained, the solid phase consisting essentially of the extracted seaweed which is depleted in moisture and some extractives, and the liquid phase comprising the organic solvent, the expelled moisture and the components dissolved therein. During step (a), the solid phase is markedly reduced in weight compared to the fresh macroalgae that was subjected to the extraction of step (a), primarily by removal of a substantial part of its internal moisture. Thus, processing volumes are reduced, product concentrations are increased, and preservability of the seaweed is improved. Overall, the invention contributes substantially to the realization of cost-effective seaweed-based biorefineries for the production of sustainable fuels and chemicals. Furthermore, by discovering that solvent-induced dehydration, the inventors have found an efficient method of mannitol isolation. The expelled water, with mannitol dissolved therein, is readily separated from the organic solvent.

The contacting of seaweed with organic solvent is occasionally performed in the context of analytical measurements, e.g. in determining the chemical composition of the macroalgae or other fundamental studies on the characteristics of the seaweed, or in the production of seaweed extracts, e.g. for (human) consumption. Such contacting is e.g. described in JP 2009/225791, JP 62286907, DE 4219360, WO 2016/157130, WO 2016/157131, WO 2017/081677, Rodriguez Gomez et al. (Abstracts of Papers, 237th ACS National Meeting, Salt Lake City, Utah, United States, Mar. 22-26, 2009 (2009), CHED-677), Sappati et al. (Journal of Food Engineering (2017), 210, 50-61), Foley et al. (J. Natural Prod. (2011), 74(9), 1851-1861), Chen et al. (Food Chem. (2008), 111(2), 503-507), Wang et al. (J. Marine Sci. Technol. (2016), 24(2), 319-328) and Wang et al. (J. Argic. Food Chem. (2012), 60, 5874-5883). The authors of each of these documents have not observed the solvent-induced dehydration of the seaweed, and consequently, none of these documents describe the further handling of the solid product, the extracted seaweed. Because of the observation of the solvent-induced dehydration, the present inventors have realized that the extracted seaweed is an excellent starting material for further biorefinery.

DETAILED DESCRIPTION

The process according to the invention is for biorefining brown macroalgae, and comprises:
(a) contacting the brown macroalgae with a solvent system comprising at least 30 wt % organic solvent, to obtain extracted macroalgae as solid residue and a liquor;
(b) biorefining the extracted macroalgae; and preferably
(c) isolating mannitol from the liquor by separation of the organic solvent and water.

In one embodiment, step (b) follows step (a) without substantial alteration of the extracted macroalgae obtained in step (a). In one embodiment, the further alteration of the extracted macroalgae obtained in step (a) before being subject to step (b) is limited to the further steps defined herein below. In one embodiment, step (c) follows step (a) without substantial alteration of the liquor obtained in step (a).

The starting material of the present process is brown macroalgae. Brown macroalgae may also be referred to as phaeophyceae or brown seaweed or brown algae. Brown macroalgae are used as source of alginate, which has a plethora of commercial uses. Brown macroalgae are the main source of alginate. Any type of brown macroalgae, as well as mixtures of different kinds may be subjected to the process according to the invention. Suitable brown macroalgae to be subjected to the process according to the invention include macroalgae belonging to the genera *Laminaria, Saccharina, Sargassum, Macrocystis, Nereocystis, Lessonia, Alaria, Ascophyllum* and *Fucus*. Preferred species of seaweed are *L. digitata* (oarweed), *S. latissima* (sugar kelp), *S. japonica* (kombu), *L. nigrescens* (giant grey weed), *M. pyrifera* (giant kelp), *A. esculenta* (winged kelp), *Fucus*

*vesiculosus* (bladderwrack) and *Ascophyllum nodosum* (knotted kelp). In one embodiment, the macroalgae comprises or is kelps (the order Laminariales). The seaweed may be naturally grown seaweed or cultivated seaweed. Typically, fresh macroalgae are used as starting material, such that the amount of pretreatment needed is limited as much as possible, although some pretreatment as defined below may optionally be performed. In particular, it is not required and not preferred that the macroalgae are dried to a large extent prior to step (a). A main advantage of the process according to the invention is that is can be applied to fresh macroalgae, without the need for costly and/or time-consuming drying steps. Thus, in a preferred embodiment, fresh macroalgae are subjected to the process according to the invention.

The seaweed used for the process according to the invention is preferably fresh macroalgae. In the context of the present invention, "fresh macroalgae" is meant to include all macroalgae having an intact cellular structure or intact cells. Thus, in the process according to the invention, preferably no measures are taken to break up the cells and/or the cell walls of the macroalgae. Such measures include extensively drying the macroalgae, e.g. by freeze-drying, heat-drying (e.g. in an oven or furnace), grinding the dried macroalgae to a powder. In a preferred embodiment, the macroalgae that are subjected to the process according to the invention have not undergone substantial rotting processes, preferably no rotting at all. For this reason already, it is preferred that the macroalgae are subjected to step (a) shortly after harvesting, such as one month after harvesting, preferably within two weeks, more preferably within one week. The inventors have surprisingly found that the process according to the invention is efficiently performed on fresh macroalgae having intact cells, e.g. from large chunks of macroalgae or even from whole macroalgae. Herein, fresh macroalgae may be defined as macroalgae not subjected to extensive drying steps, and/or as macroalgae having a water content of at least 50 wt %, preferably at least 60 wt %, more preferably 70-90 wt %, most preferably 80-85 wt %, based on total weight of the macroalgae. The macroalgae may be wet, i.e. with adherent water, or not, i.e. the adherent water may be removed, but the internal water of the macroalgae should not be removed prior to step (a).

Optionally, the macroalgae are pretreated prior to step (a). For ease of handling, the macroalgae may first be chopped to pieces (e.g. 0.5 to 30 cm in diameter). As the process according to the invention is applicable to fresh macroalgae, in one embodiment the process does not comprise a step of grinding or milling the macroalgae to a powder prior to step (a). Washing of the macroalgae with seawater and removal of large impurities (e.g. shells, sand) may be desired prior to step (a). The macroalgae may be moderately dried prior to step (a), e.g. sun-dried and/or air-dried, although this is not preferred. Thus, in the context of the invention, the terms "macroalgae" and "fresh macroalgae" are meant to include chopped macroalgae, washed macroalgae. In addition to disrupting the cellular structure of the macroalgae prior to step (a), it is also undesired to perform an aqueous extraction in the absence of organic solvent prior to step (a). One of the advantages of the process according to the invention is that any aqueous extraction can be eliminated, because the extraction of step (a) is equally capable of removing the water-soluble extractives from the macroalgae and at the same time provides the advantage of process efficiency as recited herein. In the same light, it is not required and thus undesirable to perform an aqueous extraction on the extracted seaweed after step (a), in particular in between steps (a) and (b).

Step (a)

In step (a), the macroalgae are contacted with a solvent system comprising an organic solvent to enable extraction of the macroalgae. Step (a) is the pretreatment that facilitates the downstream biorefinery of the macroalgae and may also be referred to as "dewatering", "dehydration", "extraction" or "shrinking".

The inventors have for the first time observed an as yet undescribed phenomenon that brown macroalgae experience solvent-induced dehydration by contacting the macroalgae with an organic solvent. Without being bound to a theory, it is believed that the structural matrix of the macroalgae shrinks and expels most of the moisture, including water-soluble compounds such as mannitol. Here, the term "moisture" refers to the internal moisture of the macroalgae as common in the art, not to any moisture that might adhere to the outside of the macroalgae that is subjected to step (a). Upon contacting, a solid phase and a liquid phase are obtained, the solid phase consisting essentially of the extracted seaweed (also referred to as solid residue) which is depleted in moisture and some extractives, and the liquid phase comprising the organic solvent, the expelled moisture and the components dissolved therein.

Step (a) is advantageously performed by mixing the macroalgae with the solvent system. Typically, one part (by weight) of fresh macroalgae is mixed with 0.1-10 parts by weight, preferably 0.2-5 parts by weight, most preferably 0.5-2.5 parts by weight of the solvent system. Step (a) is preferably performed at a temperature in the range of 10-100° C., more preferably 15-80° C. In one embodiment, the temperature is in the range of 10-30° C., more preferably 15-25° C. In an alternative embodiment, the temperature is in the range of 30-80° C., more preferably 45-75° C. Step (a) may be performed using any extraction technique known in the art. Conveniently, extraction is performed by washing the macroalgae with the solvent system, or by soaking the macroalgae in the solvent system. The macroalgae preferably soaks at least 1 minute in the solvent system, more preferably between 5 minutes and 600 minutes, most preferably between 10 minutes and 120 minutes. The extraction may be performed a counter-current mode. Counter-current extraction allows a reduction in the total amount of extraction solvent system needed.

The macroalgae are extracted with a solvent system, which may also be referred to as extraction liquid. The solvent system comprises one or more organic solvents. In a preferred embodiment, the solvent system is an aqueous or non-aqueous organic solvent, preferably an aqueous organic solvent. Preferably, the amount of organic solvent in the solvent system is at least 30 wt %, preferably at least 50 wt %, more preferably at least 75 wt %. Although a single organic solvent is conveniently used for practical reasons, the process according to the invention is equally workable with mixtures of organic solvents. The organic solvent(s) is preferably fully miscible with water, at all ratios. In one embodiment, the organic solvent is a ketone, an alcohol (preferably a C1-6 alcohol), an ether, an ester, or a mixture thereof, preferably an alcohol and/or a ketone. In one embodiment, the organic solvent comprises or is a ketone. In one embodiment, the organic solvent comprises or is an alcohol. In one embodiment, the organic solvent is one or more of methanol, ethanol, (iso)propanol, butanol, ethylene glycol, methoxyethanol, dimethoxyethane, dioxane and acetone. Preferably, the organic solvent is ethanol and/or acetone, more preferably ethanol or acetone. In one embodiment, the organic solvent is ethanol. In one embodiment, the organic solvent is acetone. Although optimal results are obtained with both acetone and ethanol as organic solvent, acetone may be preferred for ease of isolation of components from the extract. Acetone does not form an azeotrope with water, whereas ethanol does, and acetone has a higher volatility then ethanol, making acetone/water separation easier and less energy consuming compared to ethanol/water separation. The absence of such an azeotrope with water makes it even more surprising that the results obtained with a ketone as organic solvent at least match and at times surpass those obtained with an alcohol. This can only be explained by the phenomenon of solvent-induced dehydration which was not observed before. Further, it is especially preferred that the organic solvent is recycled, such that the cost efficiency of the overall process is further increased (the use of fresh solvent is minimized) and also in terms of durability recycling of the organic solvent is preferred. Such recycling is efficiently performed using acetone. Thus, in one preferred embodiment, the process according to the invention includes a step of recovering the organic solvent from the liquid phase originating from step (a) and reintroducing this in step (a) of the process according to the invention.

The amount of organic solvent in the solvent system is preferably governed by the final organic solvent to water weight ratio taking into account the water already present in the macroalgae. Thus, preferably the organic solvent to water weight ratio of the extraction system is in the range 10/90-90/10, preferably in the range 35/65-80/20, more preferably 40/60-55/45, most preferably about 50/50. Herein, the extraction system refers to the mixture of the macroalgae and the solvent system and thus includes the internal water present in the macroalgae. In view of the large amount of water present in the macroalgae, the solvent system would typically contain a greater part of organic solvent, such as at least 30 wt %, preferably at least 50 wt %, most preferably at least 75 wt %. Although some water may be present, the water content in the solvent system is preferably kept low, such as below 40 wt %, preferably below 30 wt % or even below 20 wt %, such as 0-30 wt % or even 5-20 wt %. Optimal results have been obtained with a solvent system comprising 10 wt % water. An especially preferred combination is the use of acetone as organic solvent, optionally in combination with some water as defined herein, at an extraction temperature in the range of 30-80° C., more preferably 45-75° C.

The extracting of step (a) yields a solid fraction and a liquid fraction. This solid fraction is subjected to step (b). The liquid fraction may also be further treated, as described below. As will be understood, separation of these fractions is part of step (a). Thus, the extracted macroalgae are separated from the extract before the it is fed to the next step in the process, typically the biorefining of step (b) as described below. Such separation may conveniently be performed by filtering the mixture of extracted macroalgae and extract (also referred to as liquor) using a filter having small enough pores to retain the extracted macroalgae, and large enough pores to allow the extract comprising extractives to pass. Typically, the pores of such a filter are between 10 μm and 10 mm in diameter, preferably between 100 μm and 1 mm. The retentate of filtration is used as starting material for biorefining.

The solid fraction, also referred to as the extracted macroalgae, consists essentially of the extracted seaweed, which is depleted in moisture and possibly extractives. The inventors found that virtually all of the alginate that is present in the macroalgae that is subjected to step (a) remains in the solid fraction and losses to the extract are negligible. Notably, the alginate content in the solid fraction could be increased from about 22 wt % to 36 wt %, based on total dry weight of the solid, because other solids, such as mannitol and ash are expelled from the macroalgae during step (a). Furthermore, during step (a) the amount of water present in the macroalgae could be reduced to about 5-25% of the original amount of water present in the fresh macroalgae, depending on the applied process conditions. Notably, this expelled moisture does not need be removed by other energy-demanding means. Most importantly, the total wet weight of the macroalgae could be reduced to less than 50% of the original wet weight by virtue of step (a), without any loss of alginate, which makes storage, transportation and further handling of the macroalgae much more efficient in terms of costs and energy.

The liquid fraction, also referred to as the extract, contains the solvent system, the expelled moisture and the extractives that are dissolved therein. The liquid fraction may further contain extractives that are soluble in the organic solvent, and which are not dissolved in the expelled moisture but extracted by the organic solvent. Because only limited amounts of water are typically present in the solvent system, the concentration of the extractives in the aqueous part of the extract is as high as possible (equal to the concentration in the macroalgae). In a preferred embodiment, one or more of the extractives are isolated from the extract.

Since step (a) reduces the moisture content and total weight of the macroalgae, and thus facilitates downstream processing, it is preferably performed shortly after harvesting of the macroalgae at sea. It may occur already on the harvesting ship, or within a few days after bringing the macroalgae harvest to shore. In a preferred embodiment, step (a) is performed within 7 days from harvesting, preferably within 3 days or even within 1 day. After step (a) is performed, the extracted macroalgae may be directly subjected to the biorefinery of step (b), or may be stored for some time, optionally after drying. In one preferred embodiment, the extracted macroalgae are stored for at least one month, preferably 1-12 months, more preferably 2-6 months, after step (a) is performed and prior to step (b).

Step (b)

Step (b) is the biorefinery of the solid fraction that is obtained in step (a). This biorefining is markedly improved over prior art biorefinery of brown macroalgae, because of the pretreatment of step (a). The volume of the macroalgae that is subjected to the biorefinery is markedly decreased, leading to less voluminous process streams, less space required for storage and less water to be removed during drying. Storing and dewatering of macroalgae may make up as much as 30% of the total costs of macroalgae biorefinery, and these costs are greatly reduced by virtue of the pretreatment according to the present invention. Thus, the process according to the invention provides a markedly improved cost efficacy and durability of the biorefinery of macroalgae.

Biorefinery step (b) may include any type of biorefinery of macroalgae as known in the art. Step (b) may involve one or more of the following: alginate isolation, hydrolysis of alginate and/or cellulose, fermentation and isolation of proteins. Such biorefinery of macroalgae is known in the art. Most preferably, step (b) involves the isolation of saccharides and/or hydrolysis to monosaccharides from the solid residue, most preferably of alginate. Biorefineries are able to process high volumes of seaweed. It is thus preferred that the amount of seaweed subjected to step (b) is at least 10 kg (total weight), preferably at least 100 kg (total weight), such as 10-10000 kg or 50-5000 kg, preferably 100-2000 kg. These amounts apply to a single batch when the process is batch-wise or semi-continuous, or to amounts per hour when the process is a continuous process.

In a preferred embodiment, the biorefinery of step (b) involves the isolation of alginate. In the context of the present invention, alginate is equitable with alginic acid and is used interchangeably. Alginate is widely applied in the food industry (e.g. as thickener) and increasingly in the textile industry. The isolation of alginate from brown macroalgae typically involves alkaline liquefaction, wherein the alginate is separated from the other structural solid components of the macroalgae. Herein the macroalgae are diluted with copious amounts of water at elevated pH, and alginate is separated from the thus obtained viscous solution by precipitation. Thus, step (b) preferably involves alkaline liquefaction. The other components of the macroalgae are typically not further used and the entire liquor is discarded as waste. In view of the diluted nature of the liquor, isolating any of the components dissolved therein it too costly and not economically viable. In order to ensure year-round supply of seaweed for alginate isolation, large amounts of the harvested macroalgae are dried and stored. These drawbacks are obviated by virtue of step (a). In a preferred embodiment, step (b) involves the isolation of alginate as defined herein and hydrolysis thereof to monosaccharides.

The pretreatment of step (a) offers several advantages for the macroalgae biorefinery process. As said above, the drying requires less energy and costs, since the starting material contains much less moisture. Secondly, further valuable components present in macroalgae are obtained in the liquid phase, the extract, that is obtained in step (a). Normally, these components are wasted with the liquor of the alkaline liquefaction. Particularly, about 80% of the mannitol comprised in the macroalgae is expelled during step (a) and ends up in the extract, from which it can be isolated and further used as deemed fit. As such, the process of the invention offers a sustainable use of brown macroalgae, wherein not only the alginate is valorised, but also further valuable components such as mannitol.

Further Steps

In an especially preferred embodiment, the extract obtained is not discarded as waste, but is further used for isolation of valuable components, in particular mannitol. This is referred to as step (c), wherein the organic solvent is separated from the aqueous phase which contains the mannitol. Mannitol may be isolated by any means known in the art, e.g. involving membrane separation and/or crystallisation. In one embodiment, step (c) involves removal of the organic solvent by evaporation at conditions which keeps the water present in the extract in liquid state. The skilled person is capable of selecting the appropriate conditions in terms of temperature and pressure to achieve selective evaporation of the organic solvent. In this context, it is preferred that the organic solvent is not capable of forming an azeotrope with water. Mannitol is a valuable compound with many applications, such as in medicine (e.g. in osmotherapy) and food products (e.g. as sweetener or coating agent). In view of its low glycemic and insulinemic indices, it is used as a low-caloric and low-cariogenic sweetener. Mannitol is not or hardly digestible by human enzymes, but is fermented by the intestinal flora. Its suitability as coating agent stems from its very low hygroscopicity. Mannitol also finds application as excipient in medical formulations, e.g. to mask the unpleasant taste of certain drugs, or as diuretic. Mannitol is also valuable as a building block or for further (chemical) modification. First of all, mannitol itself can be used as a starting material for polymer synthesis, such as reaction with isocyanides for polyurethane synthesis (e.g. rigid foams). Secondly, mannitol can be converted into isomannide, which is a valuable chiral diol suitable in the preparation of bioplastics (e.g. polyesters, polyethers, polyamides, polyurethanes).

The inventors surprisingly found that in addition to mannitol, laminarin may be isolated from the extract. Laminarin extraction was particularly efficient when a ketone, typically acetone, was used as organic solvent. It is thus preferred that step (c) involves laminarin extraction, alternative to or in addition to, preferably in addition to, mannitol isolation. Laminarin extraction can be achieved by any means known in the art. Possible application of laminarin include prebiotic, ingredient for food supplement, viscosity modifier and as precursor for glucose. Alternatively, the extract can be used as such, or possibly after demineralization and/or concentration, for fermentation to e.g. ABE (aceton, butanol, ethanol) or bio-ethanol.

The extracted macroalgae obtained in step (a) may be dried prior to the biorefinery of step (b). Such drying may also be viewed as the first step in the biorefinery of step (b). In conventional macroalgae biorefineries, such drying is performed to ensure year-round supply of the macroalgae. The same may also be performed in the context of the present invention, but since the starting material of the drying step (the extracted macroalgae) contains much less water, the drying is more efficient in terms of costs and energy consumption. The extracted and dried macroalgae would then be subjected to step (b), optionally after a certain period of storage.

In one embodiment, the process according to the invention involves removing the organic solvent from the extracted biomass obtained in step (a) and prior to step (b). Preferably, also the organic solvent is removed from the liquor obtained in step (a). Such removal of the organic solvent may be accomplished by any means known in the art, such as evaporation. In an especially preferred embodiment, the thus obtained organic solvent is recycled to step (a) to be contacted with the macroalgae.

The extracted macroalgae obtained in step (b) may, optionally after being dried, be stored for some time in order to ensure year-round availability of the macroalgae for the biorefinery of step (b). Although any type of storage as known in the art may be employed, including ensiling, the storage preferably occurs in dried form. As such, the quality of the macroalgae is not negatively affected.

EXAMPLES

The following examples are intended to illustrate the invention.

Seaweed Composition

Fresh brown seaweed used in the examples were freeze-dried and analysed for biochemical composition. The sugar composition was determined using a modified two-step hydrolysis protocol based on the NREL protocol for lignocellulose (Huijgen et al. chapter 12 in "Biotechnology Protocols for Macroalgae Research", 2017, Reddy, Wichard and Charrier (Eds), CRC Taylor & Francis, ISBN 978-1498796422). The alginate content was determined by alkaline extraction (Hernandez-Carmona et al. Journal of applied phycology, 1998, 10(6), 507-513) and its purity measured using the PHMBH assay (Kennedy and Bradshaw, Brit. Poly. J., 1984, 16, 95-101). The results are given in Table 1.

TABLE 1

Composition of brown seaweeds, in wt % based on total dry weight

| Component | Example 1 and 2 Laminaria digitata | Example 3 Saccharina latissima |
|---|---|---|
| Mannitol | 19.3 | 11.8 |
| Fucose | 1.6 | 1.8 |
| Galactose | 0.6 | 0.7 |
| Glucose | 16.5 | 8.6 |
| Xylose | 0.5 | 0.4 |
| Alginate | 22.4 | 21.4 |
| Ash | 23.4 | 35.7 |

Example 1: Ethanol Induced Dehydration of Laminaria digitata

Fresh Laminaria digitata was harvested in July 2015 by Ocean Harvest Ireland off the Irish coast. The fresh Laminaria digitata (81.2 wt % moisture) was cut into pieces of <1 cm using a standard kitchen machine. 100 g of cut seaweed was transferred to a 500 ml wide mouth Duran bottle and a solvent system of ethanol/water in different ratios was added (20-70% w/w ethanol corrected for the water present in the seaweed) so that the final volume of liquid was 400 ml including the water present in the seaweed. The seaweeds were incubated for 60 minutes at room temperature and poured over a 0.5 mm macrofilter. The ethanol in the extracts was removed using a rotary evaporator at 60° C. and 150 mbar pressure absolute. Samples from the rotavapped extract were hydrolysed in 1M sulfuric acid at 100° C. for 2 hours before measuring the glucose (from laminarin) using the o-toluidine assay (Yee and Goodwin, Analytical Chemistry 1973, 45, 2162-2165). Mannitol concentrations were measured in the original unhydrolysed rotavapped sample by the periodate method (Sanchez, Journal of agricultural and food chemistry, 1998, 46(1), 157-160). These results are depicted in Table 2.

TABLE 2

Results dehydration experiments

| E/W | Recovery wet (wt %)* | Recovery dry (wt %)* | Ash extracted (wt %)** | Glucan extracted (wt %)** | Mannitol extracted (wt %)** |
|---|---|---|---|---|---|
| 20/80 | 119.1 | 82.9 | 42.9 | 13.5 | 54.6 |
| 30/70 | 98.3 | 82.3 | 44.1 | 14.5 | 61.6 |
| 40/60 | 63.3 | 72.2 | 57.3 | 13.0 | 84.4 |
| 50/50 | 56.7 | 75.7 | 56.2 | 11.0 | 83.5 |
| 60/40 | 52.4 | 79.2 | 54.6 | 9.0 | 81.6 |
| 70/30 | 50.2 | 80.2 | 51.3 | 6.2 | 68.8 |

*Laminaria wet and dry weight after extraction and filtration
**Weight percent of the total amount of ash, glucan or mannitol present in Laminaria.

The most pronounced dehydration of the seaweed was observed in the 40-70% ethanol range. The extracts containing 20-30% ethanol were highly viscous due to the suspected presence of alginate oligomers in the extraction liquid. The extract containing 40% ethanol and more had a low viscosity. The dry weight recovery after extraction showed that most solids were extracted at 40% ethanol. At 20-30% ethanol, the volume of the extract is low due to incomplete dehydration and at 50-70% ethanol the solubility of the extractives decreases. Ash extraction is rather stable with an optimum at 40% ethanol. Laminarin (glucan) extraction decreases when the liquid contains more than 30% ethanol, most likely caused by a decreased solubility of laminarin. The majority of glucose in L. digitata is present as non-extractable cellulose. Mannitol extraction is highest when the extraction liquid contains 40-60% ethanol.

Example 2: Stepwise Extraction of Laminaria digitata 500 g of cut L. digitata was transferred to a 500 ml widemouth Duran bottle and extracted using 150 g of 90/10 (w/w) ethanol/water. After soaking and mixing for 30 minutes at room temperature the flask was capped with a 0.5 mm filter and the liquid removed by decantation. This procedure was repeated several times until the desired liquid/solid ratio for extraction was reached (see Table 3). The extracted seaweed was weighed wet and weighed after drying at 50° C. The dried seaweed was rehydrated and the alginate content was determined by alkaline extraction (Hernandez-Carmona et al. Journal of applied phycology, 1998, 10(6), 507-513) and its purity measured using the PHMBH assay (Kennedy and Bradshaw, Brit. Poly. J., 1984, 16, 95-101). The ethanol in the extracts was removed using a rotary evaporator at 60° C. and 150 mbar pressure (absolute). Samples from the rotavapped extract were hydrolysed in 1M sulfuric acid at 100° C. for 2 hours before measuring the glucose (from laminarin) using the o-toluidine assay (Yee and Goodwin, Analytical Chemistry 1973, 45, 2162-2165). Mannitol concentrations were measured in the original unhydrolysed rotavapped sample by the periodate method (Sanchez, Journal of agricultural and food chemistry, 1998, 46(1), 157-160). These results are depicted in Table 4.

TABLE 3

Stepwise extraction

| | Extraction stages * | | | | | |
|---|---|---|---|---|---|---|
| Exp. | 1 | 2 | 3 | 4 | 5 | L/S ** |
| 1 | 150 | | | | | 0.3 |
| 2 | 150 | 100 | | | | 0.5 |
| 3 | 150 | 150 | 100 | | | 0.8 |
| 4 | 150 | 150 | 150 | 100 | | 1.1 |
| 5 | 150 | 150 | 150 | 150 | 100 | 1.4 |

* Amount of solvent system added (in ml) per stage
** Overall liquid to solid ratio, calculated as weight of the solvent system (in g)/wet weight of the seaweed (in g).

TABLE 4

Results dehydration experiments

| Exp. | Recovery wet (wt %)* | Recovery dry (wt %)* | Ash extracted (wt %)** | Glucan extracted (wt %)** | Mannitol extracted (wt %)** | Alginate content (wt %)*** |
|---|---|---|---|---|---|---|
| 1 | 74.6 | 87.7 | 32.7 | 8.1 | 37.6 | 26.5 |
| 2 | 56.1 | 81.1 | 46.7 | 12.7 | 66.0 | 28.2 |

TABLE 4-continued

Results dehydration experiments

| Exp. | Recovery wet (wt %)* | Recovery dry (wt %)* | Ash extracted (wt %)** | Glucan extracted (wt %)** | Mannitol extracted (wt %)** | Alginate content (wt %)*** |
|---|---|---|---|---|---|---|
| 3 | 53.4 | 78.8 | 54.8 | 16.5 | 76.0 | 33.4 |
| 4 | 47.9 | 70.9 | 57.9 | 14.4 | 76.5 | 34.3 |
| 5 | 44.4 | 60.5 | 60.8 | 10.5 | 69.0 | 35.9 |

*Laminaria wet and dry weight after extraction and filtration.
**Weight percent of the total amount of ash, glucan or mannitol present in Laminaria.
***Alginate content of the extracted Laminaria.

The wet weight of the seaweed after extraction decreased steadily with increasing LIS. The wet seaweed has shrunk to roughly half its mass at a liquid/solid ratio of 1 kg solvent/kg wet seaweed. The dry weight kept decreasing even when there is mostly ethanol present, indicative of the extraction of ethanol-soluble extractives present in the seaweed. Mannitol and glucan extraction is completed at an L/S ratio of 0.8. After solvent removal, the mannitol concentration in the extract from experiment 3 was 38 g/l. The alginate content in the extracted laminaria is largely is increasing steadily to 36%. Recovery of alginate in the seaweed was found to be 100%, i.e. no alginate was extracted.

The use of aqueous ethanol as an extraction liquid resulted in effective dehydration of L. digitata. The expelled liquid contained most of the mannitol present in seaweed and the extracted seaweed is enriched in alginate. Balancing the effects shown here, the optimal L/S ratio with this solvent system (90 wt % ethanol in water) was found to be about 0.8-1 g/g.

Example 3: Ethanol and Acetone Induced Dehydration of Saccharina

Fresh Saccharina latissima (SL) and Alaria esculenta (AE) were harvested end of August 2016 off the Faroer Island coast. S. latissima (86.8 wt % moisture) and A. esculenta (82.6 wt % moisture) were cut into pieces of <1 cm using a standard kitchen machine. 200 g of cut seaweed was transferred to a 1 L widemouth Duran bottle. Solvent (96% ethanol or 100% acetone) and water were added to obtain 800 ml of 40 wt % aqueous ethanol and acetone (including the moisture present in the seaweed). The final liquid/solid ratio was 4 L/kg wet seaweed including the moisture present in the seaweed. The seaweeds were incubated for 60 minutes at room temperature or in a water bath at 60° C. and poured over a 0.5 mm macrofilter. The extracted seaweed was weighed wet and weighed after drying at 50° C. The dried seaweed was rehydrated and fractionated by the alkaline liquefaction method. The solvent in the extracts was removed using a rotary evaporator at 60° C. and 150 mbar pressure absolute. Samples from the solvent-free extract were hydrolyzed in 1M sulfuric acid at 100° C. for 2 hours before measuring the glucose (from laminarin) using the o-toluidine assay. Mannitol concentrations were measured in the original unhydrolysed solvent-free sample by the periodate method. The results are compared with those of example 1 and depicted in Table 5.

TABLE 5

Results dehydration experiments

| | | | Recovery wet (wt %)* | Recovery dry (wt %)* | Mannitol extracted (wt %)** | Glucan extracted (wt %)** | Alginate content (wt %)*** |
|---|---|---|---|---|---|---|---|
| SL | ethanol | RT | 62.8 | 71.0 | 70.0 | 6.5 | 33.8 |
| SL | ethanol | 60° C. | 67.4 | 70.3 | 78.6 | 13.0 | 34.7 |
| SL | acetone | RT | 61.2 | 72.4 | 65.7 | 7.2 | 31.1 |
| SL | acetone | 60° C. | 69.9 | 74.3 | 75.5 | 18.0 | 34.4 |
| AE | ethanol | RT | 83.6 | 81.4 | nd | nd | nd |
| AE | ethanol | 60° C. | 51.5 | 79.6 | nd | nd | nd |
| AE | acetone | RT | 68.5 | 79.6 | nd | nd | nd |
| AE | acetone | 60° C. | 55.8 | 80.0 | nd | nd | nd |
| LD | ethanol | RT | 63.3 | 72.2 | 84.4 | 13.0 | nd |

*Wet and dry weight after extraction and filtration
**Weight percent of the total amount of glucan or mannitol present in the seaweed.
***Alginate content of the extracted seaweed.

The wet and dry recovery of S. latissima (SL) is comparable to the recovery of L. digitata (LD) at room temperature. Using acetone at RT does not change the dehydration or extraction significantly as compared to ethanol. Extraction of S. latissima at 60° C. reduces the dehydration somewhat but this has no influence on the dry seaweed recovery. The dehydration of A. esculenta (AE) is improved at elevated temperature but eventually has no real influence on the dry seaweed recovery. For S. latissima the sugar concentration was measured in the extract and the alginate content of the extracted seaweed determined by alkaline liquefaction. Overall, mannitol extraction from S. latissima is a bit lower as compared to L. digitata. Extraction of mannitol and laminarin increased at elevated temperature. Laminarin extraction is significantly higher using acetone at 60° C. Alginate enrichment in the extracted S. latissima is highest at 60° C. with no significant difference between ethanol and acetone.

Efficient dehydration and extraction of sugars has been demonstrated for several brown seaweeds. The best results are obtained using aqueous acetone at 60° C., although ethanol and room temperature gave also satisfactory results. Results from counter-current extraction experiments using aqueous acetone at 60° C. on *Laminaria digitata* did not differ significantly with a one-pot extraction as demonstrated in examples 1, 2 and 3.

The invention claimed is:

1. A process for biorefining brown macroalgae, comprising:
   (a) contacting the brown macroalgae with a solvent system comprising at least 30 wt % of a ketone organic solvent, wherein water is expelled from the macroalgae, to obtain extracted macroalgae as solid residue and a liquor comprising expelled water;
   (b) biorefining the extracted macroalgae; and
   (c) isolating mannitol from the liquor by separation of the organic solvent and water.

2. The process according to claim 1, wherein step (b) involves one or more of alginate isolation, hydrolysis of alginate and/or cellulose, fermentation of the extracted macroalgae and isolation of proteins.

3. The process according to claim 1, wherein the extracted macroalgae are stored for at least one month prior to being subjected to step (b).

4. The process according to claim 1, wherein the brown macroalgae belongs to the genera *Laminaria, Saccharina, Sargassum, Macrocystis, Nereocystis, Lessonia, Alaria, Ascophyllum* and/or *Fucus*.

5. The process according to claim 1, wherein the organic solvent is miscible with water at all ratios.

6. The process according to claim 1, wherein the organic solvent is acetone or methyl ethyl ketone.

7. The process according to claim 1, wherein the amount of organic solvent in the solvent system is such that the organic solvent to water weight ratio, taking into account the water present in the macroalgae, is in the range of 10/90-90/10.

8. The process according to claim 1, wherein step (a) is performed at a temperature in the range of 10-100° C.

9. The process according to claim 1, wherein the solvent system comprises acetone and step (a) is performed at a temperature in the range of 30-80° C.

10. The process according to claim 1, wherein the contacting of step (a) is performed in counter-current mode.

11. The process according to claim 1, wherein the solvent system step (a) comprises at least 75 wt % organic solvent.

12. The process according to claim 1, wherein step (c) further involves the isolation of laminarin.

13. The process according to claim 1, wherein the solvent separated in step (c) is recycled to step (a).

14. The process according to claim 1, wherein the solvent system comprises at least 75 wt % acetone, and step (b) involves alkaline liquefaction, wherein alginate is separated from the extracted macroalgae.

15. The process according to claim 2, wherein step (b) involves at least alginate isolation.

16. The process according to claim 6, wherein the organic solvent is acetone.

17. The process according to claim 7, wherein the amount of organic solvent in the solvent system is such that the organic solvent to water weight ratio, taking into account the water present in the macroalgae, is in the range of 35/65-80/20.

18. The process according to claim 8, wherein step (a) is performed at a temperature in the range of 30-80° C.

19. The process according to claim 9, wherein step (a) is performed at a temperature in the range of 45-75° C.

20. The process according to claim 11, wherein the solvent system step (a) comprises 80-95 wt % organic solvent.

* * * * *